United States Patent [19]

Ban et al.

[11] Patent Number: 4,735,943
[45] Date of Patent: Apr. 5, 1988

[54] EBURNAMONINE OXIME DERIVATIVES, SALTS THEREOF, AND PHARMACEUTICAL AGENTS CONTAINING THE SAME

[75] Inventors: Masatoshi Ban, Gifu; Yutaka Baba, Iwakura; Kiichi Sawai, Funabashi, all of Japan

[73] Assignee: Sanwa Kagaku Kenkyusho Co., Ltd., Aichi, Japan

[21] Appl. No.: 740,775

[22] Filed: Jun. 3, 1985

[30] Foreign Application Priority Data

Jun. 29, 1984 [JP] Japan .................. 59-132926
Mar. 4, 1985 [JP] Japan .................. 60-41235

[51] Int. Cl.[4] .................. A61K 31/44; C07D 461/00
[52] U.S. Cl. .................. 514/253; 514/283; 514/237; 544/361; 544/125; 546/51
[58] Field of Search .................. 546/51; 514/283, 237, 514/253; 544/125, 361

[56] References Cited

U.S. PATENT DOCUMENTS

| 3,753,995 | 8/1973 | Martel et al. | 546/51 |
| 4,038,317 | 7/1977 | Wermuth et al. | 564/257 X |
| 4,045,432 | 8/1977 | Uyeda | 260/239 B |
| 4,308,399 | 12/1981 | Takacs et al. | 564/257 |
| 4,395,413 | 7/1983 | Budai et al. | 544/398 X |
| 4,425,158 | 1/1984 | Budai et al. | 71/121 |
| 4,464,535 | 8/1984 | Szántay et al. | 546/51 |
| 4,549,020 | 10/1985 | Szántay et al. | 546/51 |
| 4,551,462 | 11/1985 | Szántay et al. | 514/283 |

FOREIGN PATENT DOCUMENTS

| 0159160 | 10/1985 | European Pat. Off. | 546/51 |
| 0168197 | 1/1986 | European Pat. Off. | |
| 2085630 | 12/1971 | France | 514/283 |
| 2253502 | 8/1975 | France | |
| 0111484 | 8/1980 | Japan | 514/283 |
| 2123413 | 2/1984 | United Kingdom | 546/51 |
| 2124215 | 2/1984 | United Kingdom | 546/51 |
| 2124216 | 2/1984 | United Kingdom | 546/51 |

OTHER PUBLICATIONS

Ban, et al., Chemical Abstracts, vol. 105:79214r, p. 3072 CS, (1986).
Index Guide, Eighth Collective Index of Chemical Abstracts, p. 1580G.
Chemical Abstracts Index Guide, 1977–1981, p. 220I.

Traverso, Chemical Abstracts, vol. 51, 5762b–5863b, (1957).
Morgenstern, et al., Chemical Abstracts, vol. 67, 21475g, (1967).
"Vincamine Apovincaminic Acid Ethylester", by Kawakami et al., Pharmacometrics, vol. 10, No. 2, pp. 199–206, 1975.
"The Synthesis of Ethyl Apovincaminate", by Szasa et al., in Arzneim.-Forsch, 26, (10a), pp. 1907–1989, 1976.
"Cerebral Metabolic and Hemodynamic Activities of 1-Eburnamonine in the Anesthetized Dog", by Lacroix et al., in Arzneim.-Forsch, 29, pp. 1094–1101, 1979.

Primary Examiner—Donald G. Daus
Assistant Examiner—Diana G. Rivers
Attorney, Agent, or Firm—Armstrong, Nikaido, Marmelstein & Kubovcik

[57] ABSTRACT

There is disclosed novel eburnamonine oxime, its derivatives and salts, process for the manufacture thereof and pharmaceutical agents containing the same. The compounds are represented by the following formula.

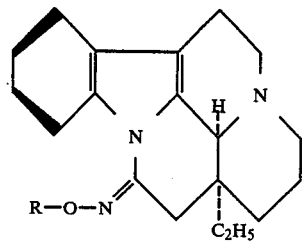

wherein R is hydrogen, alkyl, alkoxyalkyl, or oxisilanylalkyl group or a group of

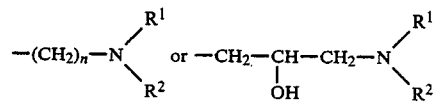

$R^1$ and $R^2$ are same or different and respectively hydrogen, alkyl having 1 to 4 carbon atoms, aryl or aralkyl group, or $R^1$ represents together with $R^2$ and the neighboring nitrogen atom a non-substituted or substituted heterocyclic ring, and n is an integer of 2 or 3.

4 Claims, No Drawings

EBURNAMONINE OXIME DERIVATIVES, SALTS THEREOF, AND PHARMACEUTICAL AGENTS CONTAINING THE SAME

BACKGROUND OF THE INVENTION

1. Field of the Invention

The present invention relates to novel heterocyclic compounds and more particularly to eburnamonine oxime derivatives, salts thereof, process for the manufacture the same as well as pharmaceutical agents containing the compound as an effective component. The compounds of the invention are represented by the general formula

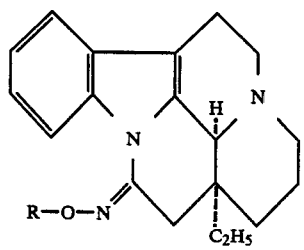

wherein R is alkyl or a group of

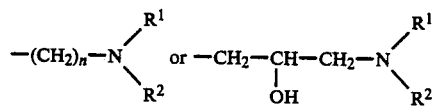

$R^1$ and $R^2$ are same or different and respectively hydrogen, alkyl having 1 to 4 carbon atoms, aryl or aralkyl group, or $R^1$ is together with $R^2$ and the neighbouring nitrogen atom a non-substituted or substituted heterocyclic ring, and n is an integer of 2 or 3.

Each of such compounds exhibits good or favorable pharmacological activities of cerebral vasodilating and metabolic activating actions and thus it is useful as an effective component for pharmaceutical agent.

2. Prior Arts

It has been known that Periwinkle (Vinca minor L. Apocyaceae) contains therein various alkaloids of vincamine, vincine, vincaminine, vincinine and the like. Among them, the vincamine has been employed as an ameliorant for curing cerebral circulatory disturbances. However, the vincamine has a disadvantage of that its effective action in a relatively short time period.

In order to overcome the disadvantage in at least some measure, various vincamine derivatives, for instance the followings have been proposed.

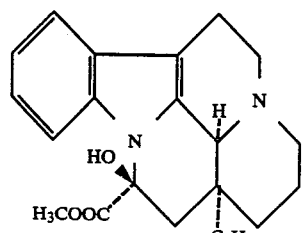

[Pharmacometpics, 10(2), 199–206, 1975]

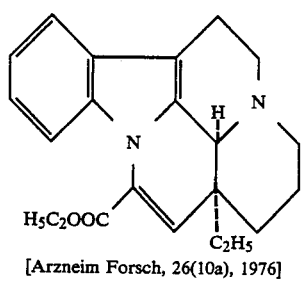

[Arzneim Forsch, 26(10a), 1976]

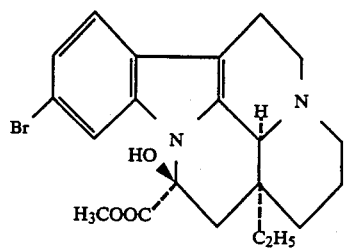

(Belgian Pat. No. 823 409 and British Pat. No. 1 492 579)

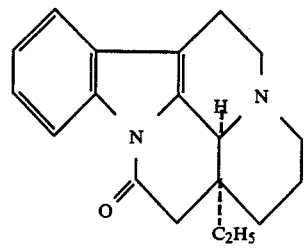

(Arzneim Forsch, 29, 1094, 1979)

Such synthetic vincamine derivatives have clinically been employed as a cerebral vasodilating or cerebral metabolism improving agent but have disadvantages in that pharmacological actions thereof are somewhat or remarkably low and a sustenance of the actions is not sufficient.

SUMMARY OF THE INVENTION

A basic matter of the invention is to overcome said disadvantages and dissolve the problems in the vincamine and the synthesized vincamine derivatives, respectively by substituting novel compounds for such known compounds, which have a chemical structure analogous with the latter.

According to one of aspects of the invention, there are provided novel eburnamonine oxime derivatives represented by following formula (I) as well as salts thereof.

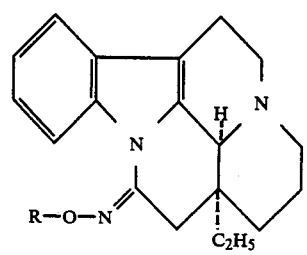

wherein R is alkyl or a group of

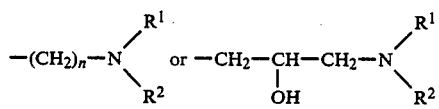

$R^1$ and $R^2$ are same or different and respectively hydrogen, alkyl having 1 to 4 carbon atoms, aryl or aralkyl group, or $R^1$ is together with $R^2$ and the neighbouring nitrogen atom a non-substituted or substituted heterocyclic ring, and n is an integer of 2 1 or 3.

In meaning of the substituent R, the term "alkyl" represents methyl, ethyl, propyl, n-butyl.

In meanings of substituents $R^1$ and $R^2$, the term "alkyl" represents methyl, ethyl, propyl, n-butyl, "aryl" represents phenyl, o- or p-methoxyphenyl, o- or p-chrolophenyl, benzoyl, "aralkyl" represents benzyl, phenylethyl, benzoylmethyl, "non-substituted heterocyclic ring" represents pyrrolidinyl, piperazinyl, morpholinyl, piperadinyl, and "substituted heterocyclic ring" represents a substituted piperazinyl wherein a substituent therefor may be an alkyl such as ethyl, propyl, isopropyl, or an aryl such as o- or p-methoxyphenyl, o- or p-chlorophenyl.

According to another aspect of the invention, there is provided a process for the manufacture of the eburnamonine oxime derivatives represented by said formula (I).

An eburnamone oxime derivative of formula (I), wherein R is alkyl or

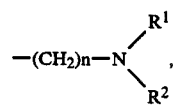

in which $R^1$, $R^2$ and n have the meanings as referred to, namely the compound represented by the formula

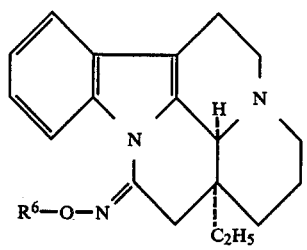

(I-a)

wherein $R^o$ is alkyl or

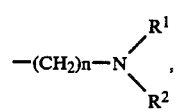

in which $R^1$, $R^2$ and n have the meanings as referred to can be prepared by reacting in an anhydrous organic solvent an eburnamonine oxime represented by the formula

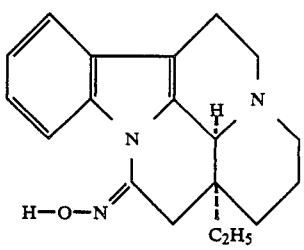

(A)

with an alkali metal hydride, further reacting in an anhydrous organic solvent the resulting alkali metal salt of said eburnamone oxime with a compound represented by the formula

$R^o$—X wherein $R^o$ has the meaning as referred to and X is halogen.

Further, an eburnamonine oxime derivative of Formula (I), wherein R is

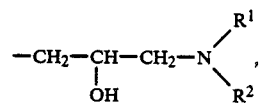

in which $R^1$ and $R^2$ have the meanings as referred to, namely the compound represented by the formula

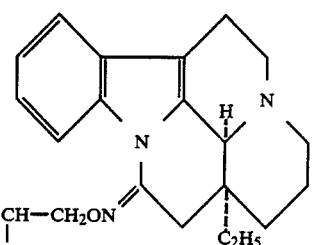

(I-b)

wherein $R^1$ and $R^2$ have the meanings as referred to, can be prepared by reacting in an anhydrous organic solvent the eburnamonine oxime shown by said formula (A) with an alkali metal hydride, reacting in an anhydrous organic solvent the resulting alkali metal salt of said eburnamonine oxime with a compound represented by the formula

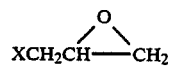

wherein X has the meaning as referred to further reacting the resulting compound with a compound represented by the formula

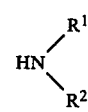

wherein $R^1$ and $R^2$ have the meanings as referred to.

As the anhydrous organic solvent, dimethylformamide, dimethylacetamide, dimethylsulfoxide and the like may be listed. A temperature between 0° and 100° C., and more particularly 0° and 60° C. is preferable for the reaction. A purification of the desired compound can be made by a chromatography or any other method known per se.

Each of the compounds represented by Formula I (Formulae I-a and I-b) can, if necessary, be converted by a method known per se to pharmaceutically acceptable acid addition salt such as hydrochloride, sulfate, phosphate, succinate, maleate, fumarate, citrate, malate, lactate, tartarate, methanesulfonate, benzoate, pamoate and the like.

The eburnamonine oxime of formula (A) as the raw material for the process according to the invention can be prepared, for instance by starting from an eburnamoninethione represented by the formula

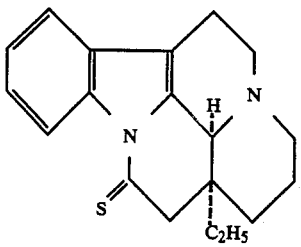
(B)

which can be obtained according to a conventional method as disclosed by Hans Behringer et al in French Pat. No. 2,253,502 and C.A. No. 84:9039(q) and reacting the compound (A) with hydroxylamine hydrochloride in an organic solvent and in the presence of an alkali metal carbonate, in accordance with another conventional method. In this case, it is preferable that an excess amount of potassium carbonate is employed as the alkali metal carbonate and the reaction is carried out at a boiling temperature of the solvent, for instance ethanol. After completion of the reaction, the solvent is removed out under a reduced pressure to concentrate the resulting reaction product and then methanol is added thereto to obtain a substance insoluble in methanol through a filtration. The substance is washed with water, dried and recrystallized from ethanol to obtain the desired eburnamonine oxime (compound A).

According to the other aspect of the invention, there is provided a pharmaceutical agent which comprises the eburnamonine derivative of formula (I) or a non-toxic salt thereof, as an effective component and which is useful as a cerebral vasolidating or cerebral metabolism improving agent.

EFFECTS OR ADVANTAGES OF THE INVENTION

According to the process of the invention, each of the eburnamonine oxime derivatives (Formula I) can be obtained with a relatively high yield and in a relatively easy manner, by starting from the eburnamonine oxime (Formula A) to be obtained by a process known per se.

The derivatives (Formula I) exhibit excellent cerebral blood flow increase and metabolic activating action and thus those are useful as amelirants on cerebral blood circultion and metabolism. At least some of the compounds (I) are superior than the conventional compounds such as vinpocetine and vinacamine derivatives in its pharmacological actions and sustenance thereof, which make a reduction of amount of dosage or dosing frequency possible. Further, a toxicity of the compounds (Formula I) is lower than known analogous compounds to increase a safety in dosage.

PREFERRED EMBODIMENTS OF THE INVENTION

The invention will now be further explained with reference to Examples for preparing Compounds (I), Test Examples showing pharmacological characters of the compounds, and the like.

REFERENCE EXAMPLE (3α,16α)-eburnamenin-14(15H)-one oxime

A mixture of 2 g (8.1 mmol) of (3α,16α)-eburnamenin-14(15H)-thione, 0.62 g (9.7 mmol) of hydroxylamine hydrochloride, 3.37 g (24.2 mmol) of potassium carbonate and 200 ml of ethanol was refluxed for 4 hours under nitrogen atmosphere and then the solvent was removed under a reduced pressure. To a residue, 100 ml of methanol was added to obtain through a filtration a substance insoluble in methanol. The substance was washed with methanol and then water, and dried to obtain 1.78 g of desired compound in the form of crude crystals. After recrystallization from ethanol, 1.61 g of colorless prisms was obtained.

Free base
Melting point: 285°–290° C. (dec.)
Yield: 64%
Mass spectrum (m/e): 309 (M+)
NMR spectrum (DMSO-$d^6$) δ ppm: 8.2–7.8 (1H, m, Ar—H), 7.3–6.8 (3H, m, Ar—H), 3.80 (1H, br s, $C_{3\alpha}$—H), 3.5–1.0 (14H, m, —$CH_2$), 0.85 (3H, br t, J=7.0 Hz, —$CH_2CH_3$).

Hydrochloride
Colorless prisms
Melting point: 288°–291° C. (dec.) (methanol)
Elementary analysis: $C_{19}H_{23}N_3O·HCl$, Calculated; C 65.98, H 6.99, N 12.15, Found; C 66.07, H 6.94, N 12.00.

EXAMPLE 2

(3α,16α)-eburnamenin-14(15H)-one O-[2-(N,N-diethylamino)ethyl]oxime 0.31 g (1.0 mmol) of (3α,16α)-eburnamenin-14(15H)-one oxime (Reference Example) was suspended under nitrogen gas atmosphere in 5 ml of dimethylformamide and then at 0° C., 55 mg (1.5 mmol) of 66% sodium hydride was added thereto to stir the mixture for 2 hours at room temperature (30° C.). To the resulting reaction mixture, 0.5 ml of diethylaminoethylchloride was added to stir for further 2 hours at room temperature. After evaporation under a reduced pressure, 5 ml of water was added and extraction was effected with chloroform three times. A combined extract was washed with water, dried with anhydrous sodium sulfate and concentrated under a reduced pressure to obtain as a yellowish oil 0.52 g of the desired compound. The crude oil was chromatographed (silica gel, triethylamine:ether:n-hexane=1:1:10−1:4:6) to obtain 0.34 g of pale yellow oil.

Free base
Yield: 84%
Mass spectrum (m/e): 408(M+)
NMR spectrum (CDCl$_3$) δ ppm: 8.5–8.2 (1H, m, Ar—H), 7.6–7.0 (3H, m, Ar—H), 4.22 (2H, t, J=6.0 Hz, —$OCH_2$—), 3.83 (1H, br s, $C_{3\alpha}$—H), 2.84 (2H, t, J=6.0 Hz, —$CH_2$—N—), 3.6–1.0 (14H, m, —$CH_2$—), 2.62 (4H, q, J=7.0 Hz, N—$CH_2CH_3$), 0.95 (6H, t, J=7.0 Hz, N—$CH_2CH_3$), 0.92 (3H, br t, J=7.0 Hz, —$C_2H_5$).

Dihydrochloride-monohydride
Colorless crystals
Melting point: 198°–201° C. (dec.) (ethanol/ether)
Elementary analysis: $C_{25}H_{36}N_4O \cdot 2HCl \cdot H_2O$, Calculated; C 60.11, H 8.07, N 11.22, Found; C 60.17, H 7.90, N 11.11.

EXAMPLE 3

(3α,16α)-eburnamenin-14(15H)-one
O-[2-(N,N-dimethylamino)ethyl]oxime 7.00 g (22.6 mmol) of (3α,16α)-eburnamenin-14(15H)-one oxime (Reference Example) was suspended in 112 ml of dried dimethylformamide. Under argon atmosphere, 2.4 g (62.2 mmol) of 60% sodium hydride was added to the suspension while cooling with ice to stir the same for 10 minutes and then the mixture was further stirred for 2 hours at room temperature. The reaction mixture was cooled with ice again to add 4.89 g (33.9 mmol) of N,N-dimethylaminoethylchloride (hydrochloride) and stir for 10 minutes, and then the resulting mixture was further stirred for 2 hours at room temperature. After evaporation, 80 ml of water and 100 ml of dichloromethane were added to separate and obtain an organic phase. The remaining water phase were extracted four times with dichloromethane. The organic phases were combined together, dried with anhydrous sodium sulfate and concentrated under a reduced pressure to obtain 11.0 g of the desired compound as a brown oil. The crude oil was chromatographed (silica gel, chroloform:methanol=40:1) to obtain 6.54 g of the compound. The compound was converted into its hydrochloride with 34.4% hydrochloric acid/ethanol solution and then the hydrochloride was recrystallized from a mixed solvent of ethanol and ether to obtain 5.50 g of dihydrochloride of the desired compound, as colorless needles.
Free base
Yield: quantitative
Mass spectrum (m/e): 380(M+)
NMR spectrum ($CDCl_3$) δ ppm: 8.47–8.20 (1H, m, Ar—H), 7.50–7.10 (3H, m, Ar—H), 4.25 (2H, t, J=6.0 Hz, —$CH_2$—O—N=), 3.82 (1H, brs, $C_{3α}$—H), 3.67–0.68 (18H, m, —$CH_2$—), 2.73 [2H, t, J=6.0 Hz, —$CH_2$—$N(CH_3)_2$], 2.35 [6H, s, —$N(CH_3)_2$], 0.92 (3H, t, J=7.5 Hz, —$CH_3$).
Dihydrochloride
Colorless needles
Melting point: 182°–194° C. (dec.) (ethanol/ether)
Elementary analysis: $C_{23}H_{32}N_4O \cdot 2HCl \cdot 3/2 H_2O$, Calculated; C 57.49, H 7.76, N 11.66, Found; C 57.38, H 7.74, N 11.67.

EXAMPLE 4

(3α,16α)-eburnamenin-14(15H)-one
O-[2-(1-pyrrolidinyl)ethyl]oxime 7.00 g (22.6 mmol) of (3α,16α)-eburnamenin-14(15H)-one oxime (Reference Example) was suspended in 112 ml of dried dimethylformamide. Under argon atmosphere, 2.49 g (62.2 mmol) of 60% sodium hydride was added to the suspension while cooling with ice to stir the same for 10 minutes and then the mixture was further stirred for 2 hours at room temperature. The reaction mixture was cooled with ice again to add 5.77 g (33.9 mmol) of pyrrolidinylethyl chloride (hydrochloride) and stir for 10 minutes, and then the resulting mixture was further stirred for 2 hours at room temperature. After evaporation under a reduced pressure, 60 ml of water and 100 ml of dichloromethane were added to the residue to dissolve the same and separately obtain an organic phase. The water phase was extracted with dichloromethane three times. The organic phases were combined together, dried with anhydrous sodium sulfate and concentrated under a reduced pressure to obtain 10.9 g of the desired compound as a brown oil. The crude oil was chromatographed (silica gel, n-hexane:ether:triethylamine=6:4:1) to obtain 8.58 g of the desired compound as a yellow oil. 7.5 g of the yello oil was dissolved in 20 ml of ethanol, 4.60 g of 34.4% hydrochloric acid/ethanol solution was added dropwise thereto and then the solvent was removed. Recrystallization was effected from a mixed solvent of ethanol and ether to obtain 6.35 g of dihydrochloride of the desired compound, as colorless needles.
Free base
Yield: 94%
Mass spectrum (m/e): 406(M+)
NMR spectrum ($CDCl_3$) δ ppm: 8.52–8.13 (1H, m, Ar—H), 7.57–7.00 (3H, m, Ar—H), 4.28 (2H, t, J=6.0 Hz, —$CH_2$—O—N=), 4.0–0.7 (18H, m, —$CH_2$—), 3.85 (1H, brs, $C_{3α}$—H), 2.87 (2H, t, J=6.0 Hz, N—$CH_2$—), 2.73–2.25 (4H, m,

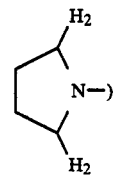

1.97–1.60 (4H, m,

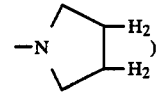

0.93 (3H, t, J=7.0 Hz, —$CH_3$).
Dihydrochloride
Colorless needles
Melting point: 183°–189° C. (dec.) (ethanol/ether)
Elementary analysis: $C_{25}H_{34}N_4O \cdot 2HCl \cdot H_2O$, Calculated; C 60.39, H 7.70, N 11.20, Found; C 60.39, H 7.79, N 11.20.

EXAMPLE 5

(3α,16α)-eburnamenin 14(15H)-one
O-{2-[4-(2-methoxyphenyl)-1-piperazinyl]ethyl}oxime 6.48 g (21.0 mmol) of (3α,16α)-eburnamenin-14(15H)-one oxime was suspended in 78 ml of dimethylformamide. Under argon atmosphere, 1.47 g (36.8 mmol) of 60% sodium hydride were added to the suspension while cooling with ice to stir the same for four hours at room temperature. To the resulting solution, 8.02 g (31.5 mmol) of 1-(2-chloroethyl)-4-(2-methoxyphenyl)-1-piperazine in 26 ml of dimethylformamide was added over a time period of 10 minutes, the mixture was stirred for two hours and then the solvent therein was removed therefrom under a reduced pressure. 100 ml of water and 200 ml of chloroform were added to extract and obtain an organic phase. The organic phase was dried with anhydrous sodium sulfate and then the solvent was removed under a reduced pressure. The residue was chromatographed (silica gel, ethyl acetate:n-hexane=1:1) to obtain 11.1 g of the desired compound as a yellow oil. The oil was further chromatographed (silica gel column, ether:n-hexane:triethylamine=1:1:0.05), resulting oil was dissolved in ethanol and converted into hydrochloride with use of hydrochloric acid/ethanol solution. The hydrochloride was recrystallized from a mixed solvent of methanol and ether to obtain 8.71 g of same as colorless needles.

Free base
Yield: quatitative
Mass spectrum (m/e): 527 (M+)
NMR spectrum (CDCl$_3$) $\delta$ ppm: 8.44–8.13 (1H, m, Ar—H), 7.51–6.59 (7H, m, Ar—H), 4.31 (2H, t, J=5.5 Hz, —CH$_2$—O—N=), 3.81 (3H, s, —OCH$_3$), 3.53–0.64 (28H, m, —CH$_2$— and —CH$_3$), 0.89 (3H, t, J=7.0 Hz, —CH$_3$).

Trihydrochloride
Colorless needles
Melting point: 220°–224° C. (dec.) (methanol/ether)
Elementary analysis: C$_{32}$H$_{41}$N$_5$O$_2$.3HCl.½H$_2$O, Calculated; C 59.48, H 7.02, N 10.84, Found; C 59.20, H 7.01, N 11.00.

EXAMPLE 6

(3α,16α)-eburnamenin-14(15H)-one O-{2-hydroxy-3-[4-(2-methoxyphenyl)-1-piperazinyl]-propyl}oxime 8.00 g (25.9 mmol) of (3α,16α)-eburnamenin-14(15H)-one oxime (Reference Example) was suspended in dried dimethylformamide. Under argon atmosphere, 1.24 g (31.0 mmol) of 60% sodium hydride were added to the suspension while cooling with ice to stir for two hours at room temperature. 4.78 g of chloromethyloxirane was added dropwise and the mixture was stirred for 2 hours at room temperature. After evaporation under a reduced pressure, 100 ml of water and 150 ml of dichloromethane were added to the residue to dissolve the same and separately obtain an organic phase. The water phase were extracted twice with dichloromethane. The organic layers were dried and evaporated to obtain an oily residue. The residue was chromatographed (silica gel column, chloroform:methanol=40:1) to obtain 9.51 g (100%) of (3α,16α)-eburnamenin-14(15H)-one O-(2,3-epoxypropyl)oximde, as a brown viscous oil.

8.00 g (21.9 mmol) of the viscous oil and 5.05 g (26.3 mmol) of 1-(2-methoxyphenyl)piperazine were dissolved in 100 ml of n-buthanol, and the solution was refluxed for one hour on an oil bath under argon atmosphere. After evaporation, the residue was purified with column chromatography (silica gel column, chloroform:methanol=40:1) to obtain 11.1 g of the desired compound, as a yellow oil.

9.50 g of the oil was dissolved in 50 ml of ethanol and 6.00 g (56.5 mmol) of 34.4% hydrochloric acid/ethanol solution was added dropwise to convert the free base to its hydrochloride. The solvent in the solution was removed under a reduced pressure and then recrystallization was effected from a mixed solvent of methanol and ether to obtain 7.20 g of the hydrochloride of desired compound, as white powder.

Free base
Yield: 91%
Mass spectrum (m/e): 557(M+)
NMR spectrum (CDCl$_3$) $\delta$ ppm: 8.50–8.20 (1H, m, Ar—H), 7.77–6.66 (7H, m, Ar—H), 4.33–4.00 (3H, m, —CH$_2$—O—N=, C$_{3\alpha}$—H), 3.82 (3H, s, —OCH$_3$), 4.00–0.70 (25H, m, —CH$_2$—, C$_{3\alpha}$—H), 0.99 (3H, t, J=7.0 Hz, —CH$_3$).

Trihydrochloride
White powder
Melting point: 171°–181° C. (dec.) (methanol/ether)
Elementary analysis: C$_{33}$H$_{43}$N$_5$O$_3$.3HCl.3/2H$_2$O, Calculated; C 57.10, H 7.12, N 10.09, Found; C 57.00, H 6.95, N 10.07.

PHARMACOLOGICAL TEST EXAMPLE 1

(Cerebral Blood Flow Increase)

Male and female mongrel dogs anesthetized with nembutal (sodium pentobarbital) were employed as subject and a blood flow in vertebral artery of those animals were measured with use of an electromagnetic rheometer. Each of testing compounds was administered to vertebral artery in a ratio of 1.0 mg/dog to determine a change in blood flow in the vertebral artery. Results are shown in following Table 1.

As seen from the Table, the compounds according to the invention have a cerebral blood flow increasing effect which is substantially equivalent to or exceeds that in conventional agent of vinpocetine, as control.

TABLE 1

| Agent or Compound | Increase in Blood Flow (%) |
|---|---|
| Reference Examples | |
| Example | 144.9 |
| 2 | 269.5 |
| 3 | 247.3 |
| 4 | 260.6 |
| 5 | 179.3 |
| 6 | 357.7 |
| Vinpocetine | 261.4 |

PHARMACOLOGICAL TEST EXAMPLE 2

(Cerebral Metabolic Activation)

According to a known method [Fujishima et al, "Rinshou-to-Kenkyu (The Clinics and Studies)" 51, 3532, 1974], both common carotid arteries of rats with an essential hypertension (SHR, male, 250–350 g, 4 to 5 animals/group) were ligated to cause a cerebral ischemia. After one hour from the ligation, each of testing compounds was orally administered in an amount of 10 mg/kg and various parameters in brain were measured at the time having lapsed 5 hours from the ligation. Results are shown in following Table 2.

From the results, it can be judged that the compounds according to the invention have an improving effect on cerebral energy metabolism, which is substantially equivalent to or exceeds that of vinpocetine as control.

TABLE 2

| Compound | Amount ($\mu$mol/g) | | |
|---|---|---|---|
| | ATP | Lactic acid | Glucose |
| Given no compound | | | |
| no treatment | 0.51 | 5.70 | 368.8 |
| treated | 0.12 | 7.05 | 377.2 |
| Reference Example | | | |
| Example | 0.20 | 7.10 | 592.3 |
| 2 | 0.36 | 4.62 | 1028.1 |
| 3 | 0.18 | 7.01 | 740.4 |
| 4 | 0.25 | 6.34 | 895.5 |
| 5 | 0.28 | 5.50 | 802.3 |
| 6 | 0.32 | 4.95 | 1010.5 |
| vinpocetine | 0.36 | 7.00 | 1121.0 |

PHARMACOLOGICAL TEST EXAMPLE 3

(Cerebral Function Protection)

To each of male d,d-mice (16–24 g, 6 to 24 animals/group), each of testing compounds was orally administered in an amount of 10 mg/kg. After 30 minutes from the administration, a cylindrical rod made of bakelite (diameter: 1 cm, weight: 36 g) was free dropped with a level height of 40 cm on a vertex of the mouse to hypnotize the same, in accordance with a method disclosed by Manaka et al ["Tyaku-no-Ayumi (The Progress in Medicines)", 104 (4), 253, 1978]. Observations were continued until a recovering reflex from the lethargy and a spontaneous motion appear to determine a reduction ratio of time period on such behavior appearances. Results are shown in following Table 3.

From the results, it can be judged that the compounds according to the invention have a cerebral function protecting effect which is substantially equivalent to or exceeds that of vinpocetine as control.

TABLE 3

| Compound | Reduction ratio (%) | |
|---|---|---|
| | time to recover sit-up reflex | time to appear spontaneous motion |
| Reference Example | | |
| Example | −12.4 (not effective) | −5.3 (not effective) |
| 2 | 54.3 | 48.7 |
| 3 | −33.0 (not effective) | −11.3 (not effective) |
| 4 | −96.1 (not effective) | −71.6 (not effective) |
| 5 | 0.4 | 6.9 |
| 6 | 23.5 | 47.2 |
| vinpocetine | 39.5 | 40.4 |

PHARMACOLOGICAL TEST EXAMPLE 4

(Depression on Blood Platelet Aggregation)

With use of a blood-plasma with excess platelets (obtained from a Wister male rat, about 250 g), a depressing effect of each testing compound to ADP and collagen aggregations was studied in vitro (3 to 5 samples/group). Results are shown in following Table 4.

From the results, it can be judged that the compounds according to the invention show a low effect on depression of ADP aggregation but a higher effect on depression of collagen aggregation, which is substantially equivalent or exceeds that of vinpocetine as control.

TABLE 4

| Compound | Final Conc. (μg/ml) | depression Ratio (%) | |
|---|---|---|---|
| | | to Collagen | to ADP |
| Reference Example | | | |
| Example | 10 | 5.4 | −1.2 (not effective) |
| 2 | 2 | 73.8 | 5.7 |
| 3 | 10 | 3.2 | 5.0 |
| 4 | 10 | 4.4 | −10.0 (not effective) |
| 5 | 10 | 9.3 | 5.5 |
| 6 | 10 | 9.5 | 6.3 |
| vinpocetine | 10 | 4.0 | −0.2 (not effective) |

PHARMACOLOGICAL TEST EXAMPLE 5

(Acceleration on Erythrocyte Deformability)

Each of testing compounds was orally administered to an amount of 10 mg/kg to Wister male rats (about 250 g, 5 animals/group). After one hour from the administration, blood sample was collected to prepare 0.1% erythrocyte suspension. An action of the compound to an erythrocyte deformability was studied in accordance with a filtration-pressure method to obtain results as shown in following Table 5.

From the results, it can be judged that the compounds according to the invention has an accelerating action on erythrocyte deformability, although it somewhat weaker than that in vinpocetine as control.

TABLE 5

| Compound | Reduction Rate in Filtering Pressure (%) |
|---|---|
| Reference Example | |
| Example | 8.3 |
| 2 | 6.0 |
| 3 | 10.2 |
| 4 | 9.3 |
| 5 | 13.2 |
| 6 | 35.1 |
| vinpocetine | 46.3 |

PHARMACOLOGICAL TEST EXAMPLE 6

(Acute Toxicity)

Each of testing compounds was orally administered to male d,d mice (8 to 10 animals/group) and an $LD_{50}$ value thereon was calculated in accordance with the conventional Litchfield-Wilcoxon method and based on mortality rate at after 72 hours. Results are shown in following Table 6.

From the results, it can be seen that a toxicity of each compound according to the invention is substantially same with that of vinpocetine as control.

TABLE 6

| Compound | $LD_{50}$ (mg/kg) |
|---|---|
| Reference Example | |
| Example | 510 |
| 2 | 611 |
| 3 | 700 |
| 4 | 532 |
| 5 | 660 |
| 6 | 560 |
| vinpocetine | 796 |

Drug Preparation Example 1 (Tablet)

Following components were added under following formula to prepare tablets in a manner known per se.

| Compound (Example 2) | 5 (mg) |
|---|---|
| Crystal cellulose | 40 |
| Magnesium stearate | 2 |
| Hydroxypropylmethylcellulose | 2 |
| Lactate | (suitable amount) |
| Total | 150 mg/tablet |

Drug Preparation Example 2 (Injection)

An isotonic solution for a compound (Example 2) was prepared in a conventional manner and with use of sodium chloride and adjusted its concentration to 2 mg/ml to prepare an injection.

Drug Preparation Example 3 (Suppository)

A compound (Example 6) was added to and uniformly dispersed in cacao fat, in following ratio and the resulting composition was subjected to a conventional molding process to prepare suppositories.

| Compound (Example 6) | 10 (mg) |
| --- | --- |
| Cacao fat | 1690 |
| Total | 1700 mg/suppository |

We claim:

1. An eburnamonine oxime compound of the formula

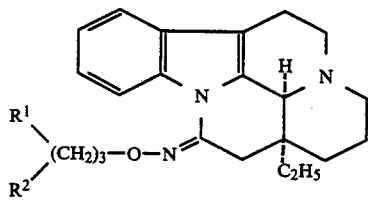

wherein $R^1$ and $R^3$ are an alkyl radical having 1 to 4 carbon atoms, respectively, or $R^1$ is a pyrrolidinyl radical together with $R^2$ and the neighbouring nitrogen atom.

2. A pharmaceutical agent which comprises as an effective component an eburnamonine oxime compound of the formula

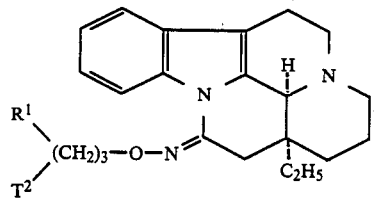

wherein $R^1$ and $R^2$ are an alkyl radical having 1 to 4 carbon atoms, respectively, or $R^1$ is a pyrrolidinyl radical together with $R^2$ and the neighbouring nitrogen atom, in an amount effective for a pharmaceutical function selected from increasing cerebral blood flow and improving cerebral metabolism;

in addition to a pharmaceutically acceptable carrier.

3. An eburnamonine oxime derivative and a non-toxic salt thereof selected from the group consisting of (3α,16α)-eburnamenin-14(15H)-one O-{2-hydroxy-3-[4-(2-methoxyphenyl)-1-piperazinyl]propyl}-oxime (3α,16α)-eburnamenin-14(15H)-one O-{2-[4-(2-methoxyphenyl)-1-piperazinyl]-ethyl}oxime and (3α,16α)-eburnamenin-14(15H)-one O-{2-hydroxy-3-[4-(2-methoxyphenyl)-1-piperazinyl]propyl}-oxime.

4. A pharmaceutical agent which comprises as an effective component, an eburnamonine oxime derivative selected from the group consisting of (3α,16α)-eburnamenin-14(15H)-one O-{2-[4-(2-methoxyphenyl)-1-piperazinyl]-ethyl}oxime and (3α,16α)-eburnamenin-14(15H)-one O-{2-hydroxy-3-[4-(2-methoxyphenyl)-1-piperazinyl]propyl}-oxime, in an amount effective for a pharmaceutical function selected from increasing cerebral blood flow and improving cerebral metabolism;

in addition to a pharmaceutically acceptable carrier.

* * * * *